United States Patent
Derwenskus et al.

(10) Patent No.: US 12,331,025 B2
(45) Date of Patent: Jun. 17, 2025

(54) METHOD FOR OBTAINING FUCOXANTHIN AND FATTY ACIDS FROM THE BIOMASS OF ALGAE

(71) Applicants: Fraunhofer-Gesellschaft zur Förderung der angewandten Forschung e.V., Munich (DE); Universität Stuttgart, Stuttgart (DE)

(72) Inventors: Felix Derwenskus, Stuttgart (DE); Ulrike Schmid-Staiger, Stuttgart (DE); Christian Bringmann, Stuttgart (DE)

(73) Assignees: Fraunhofer-Gesellschaft zur Förderung der angewandten Forschung e. V., Munich (DE); Universität Stuttgart, Stuttgart (DE)

( * ) Notice: Subject to any disclaimer, the term of this patent is extended or adjusted under 35 U.S.C. 154(b) by 967 days.

(21) Appl. No.: 17/433,959

(22) PCT Filed: Feb. 26, 2020

(86) PCT No.: PCT/EP2020/055059
§ 371 (c)(1),
(2) Date: Aug. 25, 2021

(87) PCT Pub. No.: WO2020/174019
PCT Pub. Date: Sep. 3, 2020

(65) Prior Publication Data
US 2022/0144790 A1    May 12, 2022

(30) Foreign Application Priority Data
Feb. 26, 2019   (DE) .................... 10 2019 202 570.6

(51) Int. Cl.
C07D 303/32     (2006.01)
C07C 51/43      (2006.01)
(52) U.S. Cl.
CPC ............ C07D 303/32 (2013.01); C07C 51/43 (2013.01); *C07B 2200/13* (2013.01)
(58) Field of Classification Search
CPC .... C07D 303/32; C07C 51/43; C07B 2200/13
See application file for complete search history.

(56) References Cited

U.S. PATENT DOCUMENTS 4,377,526 A    3/1983   Fujita et al.

FOREIGN PATENT DOCUMENTS

| CN | 108342420 A | 7/2018 |
|---|---|---|
| EP | 2918278 A1 | 9/2015 |
| JP | 2010011838 B1 | 1/2010 |
| JP | 2017-012135 A | 1/2017 |
| KR | 101417718 A | 7/2014 |
| KR | 20160114962 A | 10/2016 |
| WO | 2009130895 A1 | 10/2009 |
| WO | 2015101410 A1 | 7/2015 |
| WO | 2016166755 A1 | 10/2016 |
| WO | 2016175670 A1 | 11/2016 |

OTHER PUBLICATIONS

Medina, DYNA, vol. 6, No. 210, 174-178, 2019. (Year: 2019).*
Derwenskus, GCB Bioenergy, 2019, vol. 11, 335-344. (Year: 2019).*
Database WPI, Week 200974, AN 2009-Q46156, XP002798935, Method for producing fucoxanthin, involves culturing microalgae capable of producing fucoxanthin in culture medium, and extracting and separating fucoxanthin from cultured algae, 2009, 6 pages.
Database WPI, Week 201013, AN 2010-A98668, XP002798932, Producing docosahexaenoic acid (DHA) and eicosapentaenoic acid (EPA), involves preculturing marine algae chosen from prasinophytes, adding nitrogen and/or phosphorus source to culture, growing and recovering DHA and EPA from algae, 2010, 2 pages.
Database WPI, Week 201456, AN 2014-N55373, XP002798931, Purifying fucoxanthin comprises pulverizing Phaeodactylum tricornutum and Isochrysis galbana to obtain powder, adding petroleum either and mixed solvent of isopropyl alcohol and cyclohexane, extracting mixture, and concentrating, 2014, 2 pages.
Database WPI, Week 201678, AN 2016-637862, XP002798934, Collecting bioactive substance from brown algae involves crushing dried brown algae to obtain active material containing fucoxanthin and fatty acid, injecting supercritical carbon dioxide into crushed brown algae as extraction solvent, 2016, 2 pages.
Database WPI, Week 201859, AN 2018-618712, XP002798933, Use of mannitol for production of polyunsaturated fatty acids and/or fucoxanthin by cultivating diatoms and used as a carbon source to prepare medium, where diatom is cultured to produce polyunsaturated fatty acid and fucoxanthin, 2018, 4 pages.
Derwenskus et al., "Pressurized extraction of unsaturated fatty acids and carotenoids from wet Chlorella vulgaris and Phaeodactylum tricornutum biomass using subcritical liquids", GCB Bioenergy, 2019, vol. 11, pp. 335-344.
English Translation of International Search Report and Written Opinion for PCT/EP2020/055059 dated May 18, 2020, 11 pages.
Falbe et al., Entry 5,8,11,14,17-eicosapentaenoic acid:, Rompp's Chemistry Lexicon, Tape 2, Edition 10, Thieme Publishers, 1997, p. 1079.
Habeebullah et al., "Isolation of fucoxanthin from brown algae and its antioxidant activity: in vitro and 5% fish oil-in-water emulsion", J Am Oil Chem Soc, 2018, vol. 95, pp. 835-843.
Airanthi, et al. Comparative Antioxidant Activity of Edible Japanese Brown Seaweeds. Journal of Food Science. 2011; vol. 76(1):C104-C111.

(Continued)

*Primary Examiner* — D Margaret M Seaman
(74) *Attorney, Agent, or Firm* — Sheppard Mullin Richter & Hampton LLP (57) ABSTRACT

The invention relates to methods for obtaining a fucoxanthin-crystal-containing precipitate, in particular fucoxanthin crystals, in particular fucoxanthin, and a fatty-acid-containing lipid fraction, in particular fatty acids, from the biomass of algae, in particular methods for the integrated extraction and separation of fucoxanthin and fatty acids from the biomass of algae, and to the products obtained from these methods, in particular fucoxanthin crystals and fatty acids.

18 Claims, 7 Drawing Sheets

(56) References Cited

OTHER PUBLICATIONS

Foo, et al. Meeting Sustainable Development Goals: Alternative Extraction Processes for Fucoxanthin in Algae. Front. Bioeng. Biotechnol. 2021; 8:546067.

Gallego, et al. Simultaneous extraction and purification of fucoxanthin from Tisochrysis lutea microalgae using compressed fluids. J Sep Sci 2020;43:1967-1977.

Gilbert-Lopez, et al. Development of new green processes for the recovery of bioactives from Phaeodactylum tricornutum. Food Research International vol. 99, Part 3, Sep. 2017, pp. 1056-1065.

Gomez-Loredo, et al. Partition behavior of fucoxanthin in ethanol-potassium phosphate two-phase Systems. J Chem Technol Biotechnol 2014; 89: 1637-1645.

Guler, et al. A novel subcritical fucoxanthin extraction with a biorefinery approach. Biochemical Engineering Journal. vol. 153, Jan. 15, 2020, 107403.

Heo, et al. Anti-inflammatory effect of fucoxanthin derivatives isolated from Sargassum siliquastrum in lipopolysaccharide-stimulated RAW 264.7 macrophage. Food and Chemical Toxicology 50 (2012) 3336-3342.

Heo, et al. Protective effect of fucoxanthin isolated from Sargassum siliquastrum on UV-B induced cell damage. Journal of Photochemistry and Photobiology B: Biology 95 (2009) 101-107.

Hosokawa, et al. Apoptosis-Inducing Effect of Fucoxanthin on Human Leukemia Cell Line HL-60. Food Sci. Technol. Res. 1999; 5(3):243-246.

Kajikawa, et al. Stereocontrolled Total Synthesis of Fucoxanthin and Its Polyene Chain-Modified Derivative. Organic Letters. 2012; 14(3):808-811.

Kim, et al. A Potential Commercial Source of Fucoxanthin Extracted from the Microalga Phaeodactylum tricornutum. Appl Biochem Biotechnol (2012) 166:1843-1855.

Kim, et al. Fucoxanthin as a Major Carotenoid in Isochrysis aff. galbana: Characterization of Extraction for Commercial Application. J Korean Soc Appl Biol Chem (2012) 55, 477-483.

Lee, et al. Omega-3 fatty acids: cardiovascular benefits, sources and sustainability. Nature Reviews: Cardiology. 2009; vol. 6: 753-758.

Maeda, et al. Fucoxanthin from edible seaweed, Undaria pinnatifida, shows antiobesity effect through UCP1 expression in white adipose tissues. Biochemical and Biophysical Research Communications 332 (2005) 392-397.

Papadaki, et al. Recovery and Encapsualtion of Bioactive Extracts from Haematococcus Pluvialis and Phaedodactylum Tricornutum for food Applications. IOSR Journal of Environmental Science, Toxicology and Food Technology. 2016; 10 (12):53-58.

Pasquet, et al. Study on the microalgal pigments extraction process: Performance of microwave assisted extraction. Process Biochemistry. 46 (2011) 59-67.

Peng, et al. Fucoxanthin, a Marine Carotenoid Present in Brown Seaweeds and Diatoms: Metabolism and Bioactivities Relevant to Human Health. Mar. Drugs. 2011, 9, 1806-1828.

Pieber, et al. Pressurized fluid extraction of polyunsaturated fatty acids from the microalga Nannochloropsis oculata. Biomass and Bioenergy. 47 (2012) 474-482.

Sivagnanam, et al. Biological Properties of Fucoxanthin in Oil Recovered from Two Brown Seaweeds Using Supercritical CO2 Extraction. Mar. Drugs. 2015, 13, 3422-3442.

Xia, et al. Production, Characterization, and Antioxidant Activity of Fucoxanthin from the Marine Diatom Odontella aurita. Mar. Drugs. 2013, 11, 2667-2681.

Zhang, et al. An integrated biorefinery process: Stepwise extraction of fucoxanthin, eicosapentaenoic acid and chrysolaminarin from the same Phaeodactylum tricornutum biomass. Algal Research. 2018; 32:193-200.

* cited by examiner

METHOD FOR OBTAINING FUCOXANTHIN AND FATTY ACIDS FROM THE BIOMASS OF ALGAE

This application is a U.S. National Stage Application under 35 U.S.C. 371 of International Application No. PCT/EP2020/055059, filed Feb. 26, 2020, which application claims priority to German Patent Application No. 10 2019 202 570.6, filed Feb. 26, 2019. The content of each is hereby incorporated by reference in its entirety into the present disclosure.

The present invention relates to a method for obtaining a fucoxanthin-crystal-containing precipitate, in particular fucoxanthin crystals, in particular fucoxanthin, and a fatty-acid-containing lipid fraction, in particular fatty acids, from the biomass of algae, in particular methods for the integrated extraction and separation of fucoxanthin and fatty acids from the biomass of algae, as well as the products obtained from these methods, in particular fucoxanthin crystals and fatty acids.

Various macroalgae, as well as microalgae, in particular diatoms (also known as Bacillariophyta) and representatives of the Prymnesiophyceae class contain industrially relevant amounts of the carotenoid fucoxanthin (FX) as well as various, mostly polyunsaturated fatty acids (e.g., eicosapentaenoic acid EPA or docosahexaenoic acid DHA). A chemical synthesis of fucoxanthin is possible but very laborious (Kajikawa et al., 2012). EPA and DHA are usually made from fish oil (Lee et al., 2009).

Fucoxanthin is a light-harvesting pigment that occurs in the form of fucoxanthin-chlorophyll-a/c-protein complexes (FCP) in the membrane spaces of the thylakoid membranes of the algae cells, where it forwards light energy in the green to blue wavelength range to the intrinsic primary pigments in the photosystems of the cells. In addition to its coloring properties as an orange-reddish pigment, fucoxanthin is also interesting from a commercial point of view because of its health-promoting properties, which are essentially based on the structure and the functional groups of the molecule (including the epoxy group and cumulative carbon double bonds) (Peng et al., 2011). A large number of studies have already been conducted, which, among other things, document the anti-oxidative (Airanthi et al., 2011), anti-inflammatory (Heo et al., 2012), cancer-inhibiting (Hosokawa et al., 1999) and weight-reducing effects (Maeda et al., 2005) of fucoxanthin. Due to these properties, it is not only interesting from a nutritional point of view but can also be used advantageously in cosmetic products such as sunscreen (Heo and Jeon, 2009).

Depending on the algae species, the (mostly mono- and polyunsaturated) fatty acids contained in the algae are present either in the form of glycolipids and phospholipids as part of the chloroplast membrane or as storage lipids in the form of triacylglycerides (TAG). Those of the greatest economic interest are essential fatty acids such as EPA and DHA. They also have various health benefits.

Traditionally, fatty acids, such as EPA or DHA, can be obtained with both polar and nonpolar solvents or with pressure-based methods (Pieber et al., 2012). Polar solvents (ethanol, ethyl acetate, acetone) are also used to extract fucoxanthin together with other lipophilic components, such as fatty acids, at room temperature or using pressure-based methods at higher temperatures.

The traditionally used polar solvents deliver high yields of fucoxanthin but are very unselective. Thus, the extracts obtained contain very high proportions of other lipids (including fatty acids, phytosterols and other carotenoids) and have to be purified in a complex process in order to obtain high-purity fucoxanthin.

In the case of micro and macro algae, an extract is created that contains fucoxanthin, fatty acids and many other lipids. The other lipids can constitute a main part of the extract with regard to the dry matter.

To date, experts are familiar with in particular the following possibilities to separate the fatty acids (for example EPA) and the fucoxanthin in the extracted fraction to thus purify the components:

Non-polar solvents, which are not or only partially miscible with the previously used solvents (for example, hexane in combination with ethanol and water), can be used to separate the fatty acids and the fucoxanthin in the previously obtained extracts by means of liquid/liquid extraction in the two-phase system (Kim et al., 2012a, 2012b). For this purpose, large amounts of the additional solvent are necessary, and the separation of the components is usually not completely possible, so the required high purity of the two components in relation to the total dry mass of the individual fractions is not achieved.

In a method according to Kim et al. 2012a, for example, n-hexane is used to remove lipids/fatty acids from the ethanol extract, which contains both substance classes (fatty acids and fucoxanthin). It was found that fucoxanthin is almost insoluble in n-hexane and that n-hexane can therefore absorb fucoxanthin much more poorly than the aforementioned polar solvents. In addition, the extraction took three hours, which is a very long time.

By adding phosphate salts in so-called ATPS systems, the fucoxanthin can be caused to precipitate by "displacement" (Gómez-Loredo et al., 2014). The problem here is that the large amount of phosphate salt has to be removed from the system again, for example, by means of diafiltration, in order to be able to use both substances, which in turn is time-consuming and results in a further process step.

There are also studies on the chromatographic separation of the components with silica gel columns (Xia et al., 2013). Although a high degree of purity is achieved for the fucoxanthin, the process is expensive and very time-consuming.

WO 2015/101410 A1 discloses a method for the continuous extraction of fucoxanthin in which a liquid/solid extraction of the fucoxanthin takes place with at least one alkane, and the fucoxanthin is isolated from the extract by crystallization. In this process, in particular, chromatographic columns or a packed column with a fixed bed is used to isolate the fucoxanthin. What is disadvantageous about the method is that the fucoxanthin is not very pure, and the use of chromatographic columns or a packed fixed bed, in particular, is very expensive, in particular in terms of time. Furthermore, the method disclosed in WO 2015/101410 is less economical because the fatty acid-containing fraction from the algae extract is not processed further.

The present invention is based on the technical problem of obtaining both fucoxanthin and fatty acids, in particular EPA and/or DHA, in high yield, in particularly high purity and without product damage, and to thereby provide a particularly cost-effective and economically attractive method.

The present invention solves the technical problem on which it is based by providing the teaching of the independent claims.

According to the invention, a method is provided for obtaining a fucoxanthin-containing precipitate and a fatty acid-containing lipid fraction from the biomass of algae, comprising the following method steps:

a) Provision of at least one nonpolar organic solvent and biomass of algae, b) Extraction of fucoxanthin and fatty acids by means of the at least one nonpolar organic solvent provided in method step a) from the biomass of algae provided in method step a) in at least one extraction reactor unit, which is assigned to at least one first filter element, comprising, at a temperature of 60 to 150° C. and a pressure from 1.5 to 100 bar, a mixture comprising an algae extract and a biomass of algae subjected to extraction, c) Separation of the biomass of algae subjected to extraction from the mixture obtained in method step b) by means of filtration through the at least one first filter element to obtain a filtered algae extract and introduction of the filtered algae extract obtained in at least one precipitation reactor unit to which at least one second filter element is assigned, d) Lowering of the temperature of the filtered algae extract to −80 to 50° C. in the precipitation reactor unit to precipitate fucoxanthin crystals in order to obtain a mixture of fucoxanthin-crystal-containing precipitate and a fatty acid-containing algae extract fraction, e) Separation of the fucoxanthin-crystal-containing precipitate from the mixture of fucoxanthin-crystal-containing precipitate and fatty acid-containing algae extract fraction by means of filtration through the at least one second filter element to obtain a fucoxanthin-crystal-containing precipitate and a fatty acid-containing algae extract fraction, and f) Separation of a fatty acid-containing lipid fraction from the fatty acid-containing algae extract fraction by evaporating the at least one nonpolar organic solvent to obtain the fatty acid-containing lipid fraction.

The present invention therefore provides a method for, in particular, discontinuously obtaining a fucoxanthin-crystal-containing precipitate, in particular fucoxanthin, and a fatty acid-containing lipid fraction from the biomass of algae, wherein, in a first method step a), at least one nonpolar organic solvent and the biomass of algae is provided and, in a second method step b), fucoxanthin and fatty acids are extracted from the biomass of algae provided in the first method step by means of the at least one nonpolar organic solvent provided in the first method step, in particular at a temperature of 60 to 150° C. and a pressure of 1.5 to 100 bar, to obtain a mixture comprising an algae extract and a biomass of algae subjected to extraction.

In a third method step c), the biomass of algae subjected to extraction is separated from the mixture obtained in the second method step by means of filtration to obtain a filtered algae extract. In a fourth method step d), the temperature of the filtered algae extract is lowered to −80 to 50° C. to precipitate fucoxanthin crystals and thus obtain a mixture of fucoxanthin-crystal-containing precipitate and fatty acid-containing algae extract fraction.

In a fifth method step e), the fucoxanthin-crystal-containing precipitate is separated from the mixture of fucoxanthin-crystal-containing precipitate and fatty acid-containing algae extract fraction by means of filtration to obtain a fucoxanthin-crystal-containing precipitate and a fatty acid-containing algae extract fraction. In a sixth method step f), a fatty acid-containing lipid fraction is separated from the fatty acid-containing algae extract fraction by evaporation of the at least one nonpolar organic solvent to obtain the fatty acid-containing lipid fraction. The present invention provides, in particular, for the aforementioned six method steps a) to f) to be carried out in a reactor system which has at least one extraction reactor unit and at least one precipitation reactor unit downstream from the extraction reactor unit and wherein each extraction reactor unit is assigned at least one first filter element and each precipitation reactor unit is assigned at least one second filter element and wherein the at least one first filter element—viewed in the method direction from the first to the last step (method step a) to the sixth step, method step f)) —is arranged upstream from the at least one precipitation reactor unit, and the at least one second filter element is arranged downstream from the at least one precipitation reactor unit.

The present, in particular discontinuous, method according to the invention is therefore characterized, in particular, by the extraction a fucoxanthin-containing precipitate, in particular fucoxanthin, and a fatty acid-containing lipid fraction from the biomass of algae by means of at least one nonpolar organic solvent and the ability to obtain high yields and purities of fucoxanthin and fatty acids due to the reaction parameters according to the invention and the, in particular discontinuous, method using at least two filter elements so as to separate a biomass of algae obtained in a second method step and a fucoxanthin-crystal-containing precipitate obtained in a fourth method step.

The method can be carried out continuously or batchwise.

According to the invention, the extraction of fucoxanthin and fatty acids from the biomass of algae takes place at a temperature of 60 to 100° C. and a pressure of 1.5 to 100 bar in at least one extraction reactor unit to which at least one first filter element is assigned. The extraction leads to a mixture comprising an algae extract and a biomass of algae subjected to extraction. The biomass of algae subjected to extraction is removed from the mixture by filtration using the at least one first filter element. A filtered algae extract is obtained, which is introduced into at least one precipitation reactor unit to which at least one second filter element is assigned. In this at least one precipitation reactor unit, the temperature of the filtered algae extract is lowered to −80 to 50° C. in order to precipitate fucoxanthin crystals from the filtered algae extract and, accordingly, to receive a mixture of fucoxanthin-crystal-containing precipitate and a non-precipitated fatty acid-containing algae extract fraction. The fucoxanthin-crystal-containing precipitate is separated from the previously formed mixture of fucoxanthin-crystal-containing precipitate and a fatty acid-containing algae extract fraction by filtration using the at least one second filter element, wherein a fucoxanthin-crystal-containing precipitate and a fatty acid-containing algae extract fraction can be obtained. In a further method step, a fatty acid-containing lipid fraction is obtained from the fatty acid-containing algae extract fraction by evaporating the at least one nonpolar organic solvent. The fucoxanthin-crystal-containing precipitate can be further processed in at least one further method step, for example, dissolving, drying, recrystallizing, comminuting, in particular with an ultrasound treatment, or the like in order to obtain fucoxanthin crystals, in particular fucoxanthin, in particular with a defined diameter.

The method according to the invention advantageously produces fucoxanthin crystals, in particular fucoxanthin, and fatty acids, in particular DHA and EPA, in particular with a high purity and a particularly high yield. The particularly high yield of fatty acids cannot be clearly predicted because the fatty acids occur in the algae that are used in the form of glycolipids, which have a more polar character. Without being bound by theory, it is possible that thermally induced conversions of the glycolipids to free fatty acids during the extraction lead to this particularly high yield.

The method according to the invention produces the fatty acids and also the fucoxanthin in a particularly high degree of purity with both components advantageously being able to be obtained in a single method step and thus the process also being particularly economical and inexpensive. Further purification steps, in particular, can be omitted. A special advantage of the high purity of the fatty acids and the fucoxanthin crystals is their better processing. The fatty acids obtained with the method according to the invention show little or no discoloration, which is why they can be used advantageously, in particular, in the cosmetics industry.

In a particularly preferred embodiment, the method according to the invention is carried out in a reactor system set up according to the invention for carrying out the invention. A reactor system set up according to the invention comprises at least one extraction reactor unit to which at least one first filter element is assigned and at least one second precipitation reactor unit to which at least one second filter element is assigned. The reactor system preferably has an evaporation device, in particular a distillation apparatus, arranged downstream from the second filter element and connected to the precipitation reactor unit.

In a particularly preferred embodiment, at least two, in particular at least three, in particular two, in particular three, first filter elements are assigned to an extraction reactor unit.

In a particularly preferred embodiment, at least two, in particular at least three, in particular two, in particular three, second filter elements are assigned to a precipitation reactor unit.

In a particularly preferred embodiment, the at least one extraction reactor unit and the at least one precipitation reactor unit are two reactors that are spatially separated from one another and connected by a connection, in particular a fluid connection.

In a particularly preferred embodiment, the at least one extraction reactor unit and the at least one precipitation reactor unit are integrated in a reactor and represent two separate units of the reactor connected by a connection, in particular a fluid connection.

In a particularly preferred embodiment, the connection between the two reactor units is at least one hose or at least one tube.

In a particularly preferred embodiment, the connection between the two reactor units is an opening in a spatial separation device. The spatial separation device can be a wall.

In a particularly preferred embodiment, a stirrer is contained in at least one of the reactor units.

In a particularly preferred embodiment, the at least one extraction reactor unit contains a stirrer.

In a particularly preferred embodiment, the at least one precipitation reactor unit contains a stirrer.

In a particularly preferred embodiment, the at least one extraction reactor unit and the at least one precipitation unit each contain a stirrer.

In a particularly preferred embodiment, at least one of the reactor units is a fluidized bed reactor.

In a particularly preferred embodiment, the at least one extraction reactor unit is a fluidized bed reactor.

In a particularly preferred embodiment, the at least one precipitation reactor unit is a fluidized bed reactor.

In a particularly preferred embodiment, the at least one extraction reactor unit and the at least one precipitation reactor unit are fluidized bed reactors.

In a particularly preferred embodiment, at least one of the reactor units comprises a device for controlling the temperature of the reactor unit.

In a particularly preferred embodiment, the at least one extraction reactor unit comprises a device for controlling the temperature of the reactor unit.

In a particularly preferred embodiment, the at least one precipitation reactor unit comprises a device for controlling the temperature of the reactor unit.

In a particularly preferred embodiment, the at least one extraction reactor unit and the at least one precipitation reactor unit each comprise a device for controlling the temperature of the reactor unit.

In a particularly preferred embodiment, an extraction reactor unit comprises at least one inlet and at least one outlet.

In a particularly preferred embodiment, a precipitation reactor unit comprises at least one inlet and at least one outlet.

In a particularly preferred embodiment, an extraction reactor unit comprises an inlet and an outlet.

In a particularly preferred embodiment, a precipitation reactor unit comprises an inlet and an outlet.

In a particularly preferred embodiment, at least a first filter element assigned to an extraction reactor unit is in the outlet of an extraction reactor unit.

In a particularly preferred embodiment, each first filter element assigned to an extraction reactor unit is in the outlet of an extraction reactor unit.

In a particularly preferred embodiment, at least a first filter element assigned to an extraction reactor unit is in the inlet of a precipitation reactor unit.

In a particularly preferred embodiment, each first filter element assigned to an extraction reactor unit is in the inlet of a precipitation reactor unit.

In a particularly preferred embodiment, the at least one first filter element assigned to the extraction reactor unit is present in a connection between the at least one extraction reactor unit and the at least one precipitation reactor unit.

In a particularly preferred embodiment, the at least one first filter element assigned to the extraction reactor unit is present in the opening of the spatial separation device, in particular in the opening of a wall. This at least one first filter element is thus present in the connection of the at least one extraction reactor unit and the at least one precipitation reactor unit.

In a particularly preferred embodiment, the at least one first filter element is heated. This has the advantage that an early precipitation of the fucoxanthin-crystal-containing precipitate is reduced, in particular noticeably prevented, in particular completely prevented.

In a particularly preferred embodiment, the at least one first filter element has a pore size from 0.1 to 0.9 µm, in particular 0.1 to 0.5 µm, in particular 0.1 µm, in particular 0.2 µm, in particular 0.25 µm, in particular 0.5 µm, in particular 1 µm.

In a particularly preferred embodiment, the at least one first filter element is made of steel, ceramic or PTFE or a combination of these.

In a particularly preferred embodiment, the at least one first filter element is a filter which is suitable for cross-flow filtration, in particular a hollow fiber filter.

In a particularly preferred embodiment, the at least one first filter element is a sieve filter.

In a particularly preferred embodiment, the second filter element assigned to the precipitation reactor unit is present in the outlet of the precipitation reactor unit.

In a particularly preferred embodiment, the second filter element assigned to the precipitation reactor unit is present in at least one, in particular, connection between the precipitation reactor unit and subsequent devices.

In a particularly preferred embodiment, the second filter element has a pore size from 0.2 to 10 µm, in particular from 0.2 to 5 µm, in particular from 0.2 to 1 µm, in particular from 0.2 to 0.45 µm, in particular of exactly 0.2 µm, in particular exactly 0.45 µm, in particular exactly 1 µm, in particular exactly 5 µm.

In a particularly preferred embodiment, the second filter element consists of steel, ceramic or PTFE or a combination of these.

In a particularly preferred embodiment, the at least one second filter element is a filter which is suitable for cross-flow filtration, in particular a hollow fiber filter.

In a particularly preferred embodiment, the at least one second filter element is a sieve filter.

In a particularly preferred embodiment, it is provided that a device for drying, in particular for spray drying, in particular for freeze drying, is connected upstream from the extraction reactor unit.

In a particularly preferred embodiment, it is provided that a cell disruption device is connected upstream from the extraction reactor unit.

In a particularly preferred embodiment, it is provided that a cell disruption device is connected upstream from the extraction reactor unit and that a device for drying, in particular for spray drying, in particular for freeze drying, is connected downstream from the cell disruption device.

In a particularly preferred embodiment, the cell disruption device is a high-pressure homogenizer or a ball mill, in particular an agitator ball mill.

In a particularly preferred embodiment, it is provided that a distillation apparatus is connected downstream from the second filter element.

In a particularly preferred embodiment, it is provided that a solvent recycling device is connected downstream from the distillation apparatus.

In a particularly preferred embodiment, a device for further processing, in particular for comminuting, the fucoxanthin-crystal-containing precipitate is provided downstream from the second filter element. This device for further processing, in particular for comminuting, the fucoxanthin-crystal-containing precipitate can be connected regardless of the connection of a distillation apparatus, i.e., in particular in parallel with said apparatus.

In a particularly preferred embodiment, the device for comminuting the fucoxanthin-crystal-containing precipitate is a device which comminutes the fucoxanthin-crystal-containing precipitate by means of ultrasound.

In a particularly preferred embodiment, the device for comminuting the fucoxanthin-crystal-containing precipitate is a device which comminutes the fucoxanthin-crystal-containing precipitate by means of mechanical shear forces.

In a particularly preferred embodiment, there is a pressure difference between the at least one extraction reactor unit and the at least one precipitation reactor unit.

In a particularly preferred embodiment, the pressure difference across the first filter element, in particular between the at least one extraction reactor unit and the at least one precipitation reactor unit, is 1 to 99 bar, in particular 1 to 98 bar, in particular 1 to 97 bar, in particular 1 to 90 bar, in particular 1 up to 80 bar, in particular 1 to 70 bar, in particular 1 to 60 bar, in particular 5 to 99 bar, in particular 5 to 98 bar, in particular 5 to 97 bar, in particular 5 to 90 bar, in particular 5 to 80 bar, in particular 5 to 70 bar, in particular 5 to 60 bar, in particular 10 to 99 bar, in particular 20 to 98 bar, in particular 20 to 97 bar, in particular 20 to 90 bar, in particular 20 to 80 bar, in particular 20 to 70 bar, in particular 20 to 60 bar, in particular 20 to 99 bar, in particular 20 to 98 bar, in particular 20 to 97 bar, in particular 20 to 90 bar, in particular 20 to 80 bar, in particular 20 to 70 bar, in particular 20 to 60 bar.

In a particularly preferred embodiment, there is a pressure difference between the at least one extraction reactor unit and the at least one second filter element.

In a particularly preferred embodiment, the pressure difference across the second filter element, in particular between the at least one extraction reactor unit and an evaporation device, is 1 to 99 bar, in particular 1 to 98 bar, in particular 1 to 97 bar, in particular 1 to 90 bar, in particular 1 to 80 bar, in particular 1 to 70 bar, in particular 1 to 60 bar, in particular 5 to 99 bar, in particular 5 to 98 bar, in particular 5 to 97 bar, in particular 5 to 90 bar, in particular 5 to 80 bar, in particular 5 to 70 bar, in particular 5 to 60 bar, in particular 10 to 99 bar, in particular 20 to 98 bar, in particular 20 to 97 bar, in particular 20 to 90 bar, in particular 20 to 80 bar, in particular 20 to 70 bar, in particular 20 to 60 bar, in particular 20 to 99 bar, in particular 20 to 98 bar, in particular 20 to 97 bar, in particular 20 to 90 bar, in particular 20 to 80 bar, in particular 20 to 70 bar, in particular 20 to 60 bar.

In a particularly preferred embodiment, the method according to the invention has yields of 65 to 95% by weight (DM, dry matter) (yield based on the dry weight of the fatty acids in the starting material) for fatty acids.

In a particularly preferred embodiment, the method according to the invention has yields of 65 to 98% by weight (DM) (yield based on the dry weight of the EPA in the starting material) for EPA.

In a particularly preferred embodiment, the method according to the invention has yields of 30 to 75% by weight, in particular 40 to 75% by weight (DM) (yield based on the dry weight of the fucoxanthin in the starting material) for fucoxanthin.

In a particularly preferred embodiment of the method according to the invention, it is provided that the biomass of algae provided in method step a) was comminuted, in particular by cell disruption.

In a particularly preferred embodiment of the method according to the invention, the biomass of algae provided in method step a) was dried, in particular by means of spray or freeze drying, before it was provided.

In a particularly preferred embodiment of the present invention, the biomass of algae provided in method step a) was comminuted, in particular by cell disruption, and dried, in particular by means of spray or freeze drying, before it was provided.

In a particularly preferred embodiment of the present invention, the biomass of algae provided in method step a) is a particulate biomass of algae.

In a particularly preferred embodiment, it is provided that the comminution, in particular the cell disruption, of the biomass of algae is carried out by a ball mill, in particular an agitator ball mill, or by a high-pressure homogenizer, in particular by a ball mill, in particular an agitator ball mill, before it is provided in method step a).

In a particularly preferred embodiment of the present invention, it is provided that the at least one nonpolar organic solvent is an alkane, in particular an n-alkane, or a combination of different alkanes, in particular different n-alkanes.

In a particularly preferred embodiment of the present invention, it is provided that the at least one nonpolar organic solvent is pentane, hexane, heptane and/or a combination of these, in particular n-hexane, n-pentane, n-heptane and/or a combination of these, in particular cyclopentane, cyclohexane, cycloheptane and/or a combination of these.

In a particularly preferred embodiment of the present invention, it is provided that the at least one nonpolar organic solvent is hexane or heptane, in particular hexane, in particular heptane.

In a particularly preferred embodiment of the present invention, it is provided that the at least one nonpolar organic solvent is n-hexane or n-heptane, in particular n-hexane, in particular n-heptane.

In a particularly preferred embodiment, the at least one nonpolar organic solvent is mixed prior to the provision in method step a) with small amounts of at least one polar solvent, in particular 0.1 to 10% vol %, in particular 0.1 to 5 vol %, in particular 0.1 to 1 vol %, in particular 0.1 to 0.5 vol % (in each case based on the total volume of the mixture of the at least one nonpolar organic solvent and the at least one polar solvent).

In a particularly preferred embodiment, the at least one polar solvent in the mixture of the at least one nonpolar organic solvent and the at least one polar solvent is a solvent selected from the group consisting of ethanol, ethyl acetate, acetone or mixtures thereof.

Mixing the at least one nonpolar organic solvent with small amounts of at least one polar solvent prior to provision in method step a) leads, in particular and advantageously, to an increase in the yields of fucoxanthin and/or fatty acids.

In a particularly preferred embodiment of the present invention, it is provided that the biomass of algae is a biomass of macroalgae or microalgae, in particular diatoms, in particular Bacillariophyceae, in particular algae of the class Prymnesiophyceae, in particular *Phaeodactylum tricornutum*, in particular *Cylinderotheca fusiformis*, in particular *Odontella aurita*, in particular Haptophyta, in particular *Isochrysis* spec., in particular *Isochrysis aff. galbana*.

In a very particularly preferred embodiment of the present invention, it is provided that the biomass of algae is a biomass of algae with *Phaeodactylum tricornutum*.

In a particularly preferred embodiment, the method for obtaining a fucoxanthin-containing precipitate and a fatty acid-containing lipid fraction from a biomass of algae is a method for discontinuously obtaining a fucoxanthin-containing precipitate and a fatty acid-containing lipid fraction from a biomass of algae.

In a particularly preferred embodiment, the method according to the invention provides that the temperature in method step b) is 100 to 120° C., in particular exactly 100° C.

In a particularly preferred embodiment of the present invention, the temperature in method step b) is 70 to 120° C., in particular 70 to 100° C., in particular 70 to 95° C., in particular 70 to 90° C., in particular 70 to 80° C., in particular exactly 70° C.

In a particularly preferred embodiment of the present invention, the temperature in method step b) is 80 to 150° C., in particular 80 to 120° C., in particular 80 to 100° C., 85 to 150° C., in particular 85 to 120° C., in particular 85 to 100° C., in particular 90 to 150° C., in particular 90 to 100° C., in particular exactly 80° C., in particular exactly 90° C., in particular exactly 95° C.

In a particularly preferred embodiment, it is provided that the pressure in method step b) is 3 to 100 bar, in particular 5 to 100 bar, in particular 10 to 100 bar, in particular 15 to 100 bar, in particular 20 to 100 bar, in particular 25 to 100 bar, in particular 30 to 100 bar, in particular 40 to 100 bar, in particular 50 to 100 bar, in particular 60 to 100 bar, in particular 70 to 100 bar, in particular 1.5 to 90 bar, in particular 1.5 to 80 bar, in particular 1, 5 to 70 bar, in particular 1.5 to 60 bar, in particular 1.5 to 50 bar, in particular 1.5 to 40 bar, in particular 1.5 to 30 bar, in particular 1.5 to 25 bar, in particular 1.5 to 20 bar, in particular 1.5 to 15 bar, in particular 1.5 to 10 bar, in particular 1.5 to 5 bar, in particular 1.5 to 3 bar, in particular 3 to 90 bar, in particular 3 to 80 bar, in particular 3 to 70 bar, in particular 3 to 60 bar, in particular 3 to 50 bar, in particular 3 to 40 bar, in particular 3 to 30 bar, in particular 3 to 25 bar, in particular 3 to 20 bar, in particular 3 to 15 bar, in particular 3 to 10 bar, in particular 3 to 5 bar, in particular 5 to 90 bar, in particular 5 to 80 bar, in particular 5 to 70 bar, in particular 5 to 60 bar, in particular 5 to 50 bar, in particular 5 to 40 bar, in particular 5 to 30 bar, in particular 5 to 25 bar, in particular 5 to 20 bar, in particular 5 to 15 bar, in particular 5 to 10 bar.

In a very particularly preferred embodiment, it is provided that the pressure in method step b) is 100 bar.

The pressure used in method step b) can, in particular, be used synergistically to effect the extraction according to method step b) and, according to a particular embodiment, to obtain a filtered algae extract via the first filter element and to separate a fucoxanthin-containing precipitate via the second filter element and to obtain a fatty acid-containing algae extract fraction.

In a particularly preferred embodiment, the pressure applied in method step b) can be used to obtain a filtered algae extract via the first filter element and/or to separate a fucoxanthin-containing precipitate via the second filter element and to obtain a fatty acid-containing algae extract fraction.

In a particularly preferred embodiment, the pressure applied in method step b) can be used to obtain a filtered algae extract via the first filter element and to separate a fucoxanthin-containing precipitate via the second filter element and to obtain a fatty acid-containing algae extract fraction.

In a particularly preferred embodiment, it is provided that the residence time in the extraction reactor unit in method step b) is 1 to 60 minutes, in particular 1 to 45 minutes, in particular 1 to 30 minutes, in particular 1 to 25 minutes, in particular 1 to 20 minutes, in particular 1 to 15 minutes, in particular 1 to 10 minutes, in particular 1 to 5 minutes.

In a very particularly preferred embodiment, it is provided that the residence time in the extraction reactor unit in method step b) is 1 to 5 minutes.

The particularly short residence times in method step b) mean that, compared to previously known methods, there is less product damage from fatty acids and/or fucoxanthin and/or the fatty acid-containing lipid fraction and/or the fucoxanthin-crystal-containing precipitate have a higher purity.

In a particularly preferred embodiment of the present invention, it is provided that method step b) is carried out in a batch mode of operation.

In a particularly preferred embodiment, the method according to the invention provides that method step b) is repeated at least once, in particular at least twice, in particular at least three times, in particular at least four times, before method step c) is carried out.

In a particularly preferred embodiment of the present invention, it is provided that the algae extract obtained in method step b) comprises further carotenoids, polyphenols and/or phytosterols. In particular, it is provided that the aforementioned substances, i.e., further carotenoids, polyphenols and/or phytosterols, are obtained in a particularly preferred embodiment of the present invention with the fatty acid-containing lipid fraction in method step f), i.e., they are present in the fatty acid-containing lipid fraction.

In a particularly preferred embodiment, the at least one nonpolar organic solvent is preheated prior to the method step b) in a method step b0) to the temperature required in method step b), in particular in the extraction reactor unit, preferably in a separate device that is upstream from the extraction reactor unit and connected to it.

In a particularly preferred embodiment, the at least one nonpolar organic solvent is preheated prior to the method step b) in a method step b0) in the precipitation reactor unit, which is preferably equipped with a temperature control device, and then transferred to the extraction reactor unit.

In a particularly preferred embodiment of the present invention, the pressure is reduced in method step c) after the extraction has been carried out in method step b).

In a particularly preferred embodiment, after the extraction has been carried out in method step b), the pressure is reduced in method step c) to 1 to 30 bar, in particular 1 to 20 bar, in particular 1 to 15 bar, in particular 1 to 10 bar, in particular 1 to 5 bar, in particular 1 to 3 bar, in particular 1 to 2 bar, in particular 1 to 1.5 bar, in particular 1.5 to 30 bar, in particular 1.5 to 20 bar, in particular 1.5 to 15 bar, in particular 1.5 to 10 bar, in particular 1.5 to 5 bar, in particular 1.5 to 3 bar, in particular 1.5 to 2 bar, in particular 2 to 30 bar, in particular 2 to 20 bar, in particular 2 to 15 bar, in particular 2 to 10 bar, in particular 2 to 5 bar, in particular 2 to 3 bar, in particular 3 to 30 bar, in particular 3 to 20 bar, in particular 3 to 15 bar, in particular 3 to 10 bar, in particular 3 to 5 bar, in particular 1 bar, in particular 2 bar, in particular 3 bar, in particular 5 bar, in particular 10 bar, in particular 20 bar.

In a particularly preferred embodiment, after the extraction in method step b) has been carried out, the pressure is reduced in method step c) to 0 to 10 bar, in particular 0 to 5 bar, in particular 0 to 3 bar, in particular 0 to 2 bar, in particular 0 to 1.5 bar, in particular 0 bar.

In a very particularly preferred embodiment, after the extraction in method step b) has been carried out, the pressure is reduced to 30 bar in method step c).

The pressure used for the extraction in method step b) can also be used to effect the filtrations in method steps c) and/or e) in an energetically meaningful manner via the pressure differences at the at least one first and/or at least one second filter element. In particular, the pressure according to method step b) can be used to effect the filtrations in method steps c) and e), in particular in an energetically meaningful manner via the pressure differences at the at least one first and at least one second filter element.

In a particularly preferred embodiment of the present invention, the pressure is reduced in method step e) after the precipitation has been carried out in method step d).

In a particularly preferred embodiment, the pressure in the precipitation reactor unit during method step d) is 1 to 30 bar, in particular 1 to 20 bar, in particular 1 to 15 bar, in particular 1 to 10 bar, in particular 1 to 5 bar, in particular 1 to 3 bar, in particular 1 to 2 bar, in particular 1 to 1.5 bar, in particular 1.5 to 30 bar, in particular 1.5 to 20 bar, in particular 1.5 to 15 bar, in particular 1.5 to 10 bar, in particular 1.5 to 5 bar, in particular 1.5 to 3 bar, in particular 1.5 to 2 bar, in particular 2 to 30 bar, in particular 2 to 20 bar, in particular 2 to 15 bar, in particular 2 to 10 bar, in particular 2 to 5 bar, in particular 2 to 3 bar, in particular 3 to 30 bar, in particular 3 to 20 bar, in particular 3 to 15 bar, in particular 3 to 10 bar, in particular 3 to 5 bar, in particular 1 bar, in particular 2 bar, in particular 3 bar, in particular 5 bar, in particular 10 bar, in particular 20 bar, in particular 30 bar.

In a very particularly preferred embodiment, the pressure in the precipitation reactor unit during method step d) is 30 bar.

In a particularly preferred embodiment, the pressure in the precipitation reactor unit is reduced during method step d).

In a particularly preferred embodiment, the pressure in the precipitation reactor unit during method step d) is 1 to 20 bar, in particular 1 to 15 bar, in particular 1 to 10 bar, in particular 1 to 5 bar, in particular 1 to 3 bar, in particular 1 to 2 bar, in particular 1 to 1.5 bar, in particular 1.5 to 20 bar, in particular 1.5 to 15 bar, in particular 1.5 to 10 bar, in particular 1.5 to 5 bar, in particular 1.5 to 3 bar, in particular 1.5 to 2 bar, in particular 2 to 20 bar, in particular 2 to 15 bar, in particular 2 to 10 bar, in particular 2 to 5 bar, in particular 2 to 3 bar, in particular 3 to 20 bar, in particular 3 to 15 bar, in particular 3 to 10 bar, in particular 3 to 5 bar, in particular 1 bar, in particular 2 bar, in particular 3 bar, in particular 5 bar, in particular 10 bar, in particular 20 bar.

In a very particularly preferred embodiment, the pressure in the precipitation reactor unit is reduced to 3 bar during method step d).

In a particularly preferred embodiment, the pressure in the precipitation reactor unit is 30 bar at the beginning of method step d) and is reduced to 3 bar during method step d).

In a particularly preferred embodiment, after the precipitation has been carried out in method step d) in method step e), the pressure is reduced to 1 to 20 bar, in particular 1 to 15 bar, in particular 1 to 10 bar, in particular 1 to 5 bar, in particular 1 to 3 bar, in particular 1 to 2 bar, in particular 1 to 1.5 bar, in particular 1.5 to 20 bar, in particular 1.5 to 15 bar, in particular 1.5 to 10 bar, in particular 1.5 to 5 bar, in particular 1.5 to 3 bar, in particular 1.5 to 2 bar, in particular 2 to 20 bar, in particular 2 to 15 bar, in particular 2 to 10 bar, in particular 2 to 5 bar, in particular 2 to 3 bar, in particular 3 to 20 bar, in particular 3 to 15 bar, in particular 3 to 10 bar, in particular 3 to 5 bar, in particular 1 bar, in particular 2 bar, in particular 3 bar, in particular 5 bar, in particular 10 bar, in particular 20 bar.

In a particularly preferred embodiment, after the precipitation in method step d) has been carried out, the pressure in method step e) is reduced to 0 to 10 bar, in particular 0 to 5 bar, in particular 0 to 3 bar, in particular 0 to 2 bar, in particular 0 to 1.5 bar, in particular 0 bar.

In a very particularly preferred embodiment, after the precipitation has been carried out in method step d), the pressure is reduced to 0 bar in method step e).

In a particularly preferred embodiment, it is provided that the filtration of method step c) is a cross-flow filtration.

In a particularly preferred embodiment, it is provided that the filtration of method step c) is a screen filtration.

In a particularly preferred embodiment, it is provided that the temperature in method step d) is reduced to −80 to 40° C., in particular −60 to 50° C., in particular −60 to 40° C., in particular −40 to 50° C., in particular −40 to 40° C., in particular −20 to 50° C., in particular −20 to 40° C., in particular 0 to 50° C., in particular 0 to 40° C., in particular 5 to 50° C., in particular 5 to 40° C., in particular 10 to 50° C., in particular 10 to 40° C., in particular 15 to 50° C., in particular 15 to 40° C.

In a particularly preferred embodiment, it is provided that the residence time in the precipitation reactor unit in method step d) is 1 to 60 minutes, in particular 1 to 45 minutes, in particular 1 to 30 minutes, in particular 1 to 20 minutes, in particular 1 to 15 minutes, in particular 1 to 10 minutes, in particular 1 to 5 minutes.

The particularly short residence times in method step d) mean that, compared to previously known methods, there is less product damage from fatty acids and/or fucoxanthin and/or the fatty acid-containing lipid fraction and/or the fucoxanthin-crystal-containing precipitate have a higher purity.

In a particularly preferred embodiment of the present invention, it is provided that method step d) is carried out in a semi-continuous mode of operation, in particular in a countercurrent mode of operation.

In a particularly preferred embodiment of the present invention, it is provided that method step d) is carried out in a batch mode of operation.

In a particularly preferred embodiment, it is provided that method steps b) and d) are carried out in a batch mode of operation.

In a particularly preferred embodiment, it is provided that method step b) is carried out in a batch mode of operation and method step d) in a semi-continuous mode of operation, in particular in a countercurrent mode of operation.

In a particularly preferred embodiment of the present invention, it is provided that the fucoxanthin-crystal-containing precipitate is separated in method step e) by means of overpressure, underpressure or vacuum-assisted filtration.

In a particularly preferred embodiment, it is provided that the filtration in method step e) is a cross-flow filtration.

In a particularly preferred embodiment, it is provided that the filtration in method step e) is a screen filtration.

In a particularly preferred embodiment, the method according to the invention provides that the at least one nonpolar organic solvent evaporated in method step f) is liquefied in an additional method step g) and that the liquefied, at least one nonpolar organic solvent is provided again in method step a).

In a particularly preferred embodiment, the method according to the invention provides that method step g) is carried out in a device for recycling the solvent.

In a particularly preferred embodiment, the present invention also relates to fucoxanthin crystals which are producible, in particular produced, by a method according to the invention.

In a particularly preferred embodiment, the present invention also relates to the fatty acids, in particular EPA and/or DHA, which are producible, in particular produced, by a method according to the invention.

In a particularly preferred embodiment, the fatty acid-containing lipid fraction obtained in method step f) has 40 to 90% by weight, in particular 45 to 75% by weight, and comprises, fatty acids (based on the total weight of the dry matter).

In a particularly preferred embodiment, the fatty acid-containing lipid fraction consists substantially of fatty acids, and preferably consists of these.

In a particularly preferred embodiment, the fatty acid-containing lipid fraction obtained in method step f) has 10 to 50% by weight, in particular 20 to 35% by weight, EPA (based on the total weight of the dry matter).

In a particularly preferred embodiment, the fatty acid-containing lipid fraction obtained in method step f) has 50 to 70% by weight, in particular 55 to 65% by weight, EPA (based on the total weight of the dry matter of fatty acids in the fatty acid-containing lipid fraction).

In a particularly preferred embodiment, the fatty acid-containing lipid fraction obtained in method step f) has 50 to 70% by weight, in particular 55 to 65% by weight, DHA (based on the total weight of the dry matter of fatty acids in the fatty acid-containing lipid fraction).

In a particularly preferred embodiment, the fatty acid-containing lipid fraction obtained in method step f) has more EPA than DHA, in particular 1.2 times, in particular 1.5 times, in particular 2 times, in particular 5 times, in particular 10 times the amount of EPA compared to DHA (based on the total weight of EPA and DHA). This is particularly advantageous when higher proportions of EPA are required. When using the previously known source for EPA and DHA, i.e., fish oil, both must be separated from one another with means of a complex chromatographic process.

In a particularly preferred embodiment, the fatty acid-containing lipid fraction obtained in method step f) has an oily consistency.

In a particularly preferred embodiment, the fucoxanthin-crystal-containing precipitate obtained in method step e) has 50 to 100% by weight, in particular 60 to 99.999% by weight, fucoxanthin, in particular fucoxanthin crystals (based on the total weight of the dry matter).

It is provided, in particular in the preferred embodiment according to the invention, that the purity of the fucoxanthin crystals, i.e., the proportion of fucoxanthin crystals in the fucoxanthin crystal in the fucoxanthin-crystal-containing precipitate, is influenced by varying the length of the residence time, the rate of cooling or both parameters in method step d).

In a further preferred embodiment, it can be provided that the diameter of the fucoxanthin crystals obtained in the fucoxanthin-crystal-containing precipitate can be influenced by varying the length of the residence time, the rate of cooling or both parameters in method step d).

In one embodiment of the present invention, the fucoxanthin crystals contained in the fucoxanthin-crystal-containing precipitate are in the form of agglomerates, for example, a size of 10 to 100 µm, in particular 10 to 80 µm, in particular 10 to 70 µm, in particular 10 to 50 µm, in particular 10 to 25 µm, in particular 20 to 100 µm, in particular 20 to 80 µm, in particular 20 to 70 µm, in particular 20 to 50 µm, in particular 20 to 25 µm, in particular 30 to 80 µm, in particular 30 to 70 µm, in particular 30 to 50 µm. In particularly preferred embodiments, ultrasound can be used to convert these agglomerates into individual crystals.

In a particularly preferred embodiment, the fucoxanthin crystals are obtained from the fucoxanthin-crystal-containing precipitate by comminuting the fucoxanthin-crystal-containing precipitate.

In a particularly preferred embodiment, it is provided that the fucoxanthin-crystal-containing precipitate is comminuted by means of ultrasound to obtain fucoxanthin crystals.

In a particularly preferred embodiment, it is provided that the fucoxanthin-crystal-containing precipitate is comminuted by means of mechanical shear forces to obtain fucoxanthin crystals.

In a particularly preferred embodiment, it is provided that the fucoxanthin-crystal-containing precipitate is recrystallized to obtain fucoxanthin crystals.

In a particularly preferred embodiment of the present invention it is provided that the fucoxanthin crystals contained in the fucoxanthin-crystal-containing precipitate in method step e) have a diameter of 0.1 to 10 µm, in particular 0.5 to 10 µm, in particular 1 to 10 µm, in particular 2 to 10 µm, in particular 3 to 10 µm, in particular 4 to 10 µm, in particular 5 to 10 µm, in particular 6 to 10 µm, in particular 8 to 10 µm, in particular 0.1 to 8 µm, in particular 0.1 to 6 µm, in particular 0.1 to 4 µm, in particular 0.1 to 2 µm, in particular 0.1 to 1 µm, in particular 0.5 to 8 µm, in particular 0.5 to 6 µm, in particular 0.5 to 4 µm, in particular 0.5 to 2 µm, in particular 0.5 to 1 µm, in particular 1 to 9 µm, in particular 1 to 8 µm, in particular 1 to 6 µm, in particular 1 to 5 µm, in particular 1 to 4 µm, in particular 1 to 2 µm, in particular 3 to 8 µm, in particular 3 to 6 µm, in particular 3 to 5 µm, in particular 3 to 4 µm.

In connection with the present invention, "biomass of algae" is understood to refer to a material of biological origin which comprises algae, in particular macroalgae, in particular microalgae, and in particular consists substantially of them, in particular consists of them.

In connection with the present invention, "the biomass of algae subjected to extraction" is understood to refer to a biomass of algae from which substances have been removed by means of extraction. In particular, it is understood to refer to the materials which do not dissolve in the solvent used.

In connection with the present invention, an "algae extract" is understood to refer to a composition of at least one nonpolar solvent and substances from the biomass of algae dissolved in the solvent.

In connection with the present invention, a "filtered algae extract" is understood to refer to an algae extract which has been subjected to a separation, in particular a filtration.

In connection with the present invention, a "fucoxanthin-crystal-containing precipitate" is understood to refer to a material precipitated from a filtered algae extract, which comprises fucoxanthin crystals, in particular substantially consists of them, in particular consists of them. In particular, the fucoxanthin-crystal-containing precipitate can comprise agglomerates of fucoxanthin crystals, in particular consist substantially of them, in particular consist of them.

In connection with the present invention, a "fatty acid-containing algae extract fraction" is understood to refer to an algae extract fraction which comprises fatty acids, in particular consists substantially of them, in particular consists of them, and which has, for the most part, in particular completely been separated from precipitated fucoxanthin crystals.

In connection with the present invention, a "fatty acid-containing lipid fraction" is understood to refer to a fraction which comprises lipids, including fatty acids, in particular consists substantially of them, in particular consists of them. In particular, the fatty acid-containing lipid fraction can comprise fatty acids, in particular consist substantially of them, in particular consist of them. This fraction can also be referred to as algae oil.

In connection with the present invention, a "filter element" is understood to refer to a device which is suitable for filtering. This device can be designed in any configuration, shape, size or type, as long as it is suitable for filtering.

In connection with the present invention, a "first filter element" is understood to refer to a filter element which is able to separate a biomass of algae that has been subjected to extraction from an algae extract obtained by extracting fucoxanthin and fatty acids by means of at least one nonpolar organic solvent, wherein the algae extract, as a filtered algae extract, represents the permeate, and the biomass of algae subjected to extraction represents the retentate.

In connection with the present invention, a "second filter element" is understood to refer to a filter element which is able to separate a fucoxanthin-crystal-containing precipitate from a fatty acid-containing algae extract fraction, wherein the fucoxanthin-crystal-containing precipitate and the fatty acid-containing algae extract fraction represent the permeate.

In connection with the present invention, an "extraction reactor unit" is understood to refer to a device which serves as a reaction space for a solution reaction, i.e., an extraction.

In connection with the present invention, a "precipitation reactor unit" is understood to refer to a device which serves as a reaction space for a precipitation reaction, i.e., a precipitation.

In connection with the present invention, a "batch mode" is understood to refer to a discontinuous mode of operation of a reactor unit, i.e., the starting materials are added to the almost empty, in particular empty, reactor unit, and the products are removed from the reactor unit after a certain residence time.

In connection with the present invention, "separating" is understood to mean that part of a mixture is spatially separated from the remaining part or parts and that the part of the mixture is therefore no longer physically in contact with the remaining part or parts.

In connection with the present invention, "discontinuous receipt" is understood to mean that the method according to the invention is such that no continuous product stream leads to the receipt of the products according to the invention but that these are obtained in distinct quantity units.

In connection with the present invention, "extraction" is understood to mean that one or more substances from a material or mixture of substances are dissolved by means of an extractant, i.e., a solvent, i.e., they dissolve in the extractant.

In connection with the present invention, pressure is understood to refer to the pressure after the subtraction of the atmospheric pressure.

In connection with the present invention, a reducing or reduction of a first pressure from a first pressure range specified for a specific method step to a second pressure which falls within a further, second pressure range specified for a subsequent, further second method step, means that the first pressure used in the method according to the invention is selected from the first pressure range and is reduced to a different, namely lower, pressure selected from the second further pressure range.

In connection with the present invention, a reduction of the pressure is preferably understood to mean that the pressure is reduced to >0 bar.

In connection with the present invention, a reduction of the pressure is preferably understood to mean that the pressure is reduced to 0 bar.

In connection with the present invention, the specified pressure in bar can also be specified in Pa. One bar equals 100,000 Pa (0.1 MPa).

In connection with the present invention, the relative spatial information provided in relation to the reactor system used in the method according to the invention, in particular "upstream from" and "downstream from," is to be understood in the direction of the method according to the invention, i.e., from method step a) to method step f).

Further advantageous embodiments result from the dependent claims.

The invention is explained in more detail with the help of the following examples and the associated figures.

The figures show:

FIG. 2: a representation of UHPLC chromatograms (A) and mass spectra (B) of a commercial analytical fucoxanthin standard (≥95%, both at the top) and a fucoxanthin-crystal-containing precipitate obtained according to the invention from *P. tricornutum* (≥95%, both at the bottom), FIG. 4: a scanning electron micrograph (SEM) of the fucoxanthin-containing precipitate obtained according to the invention with fucoxanthin crystal agglomerates (A) and individual fucoxanthin crystals (B and C).

LIST OF REFERENCE SIGNS

10 Extraction reactor unit
20 Precipitation reactor unit
11 First filter element
21 Second filter element
30 Distillation apparatus
40 Solvent recycling device
51 Device for the cell disruption of the biomass of algae
52 Device for drying the biomass of algae
A1 Biomass of algae
P1 Fucoxanthin-containing precipitate
P2 Fatty acid-containing lipid fraction

EXAMPLES

Figure 1:
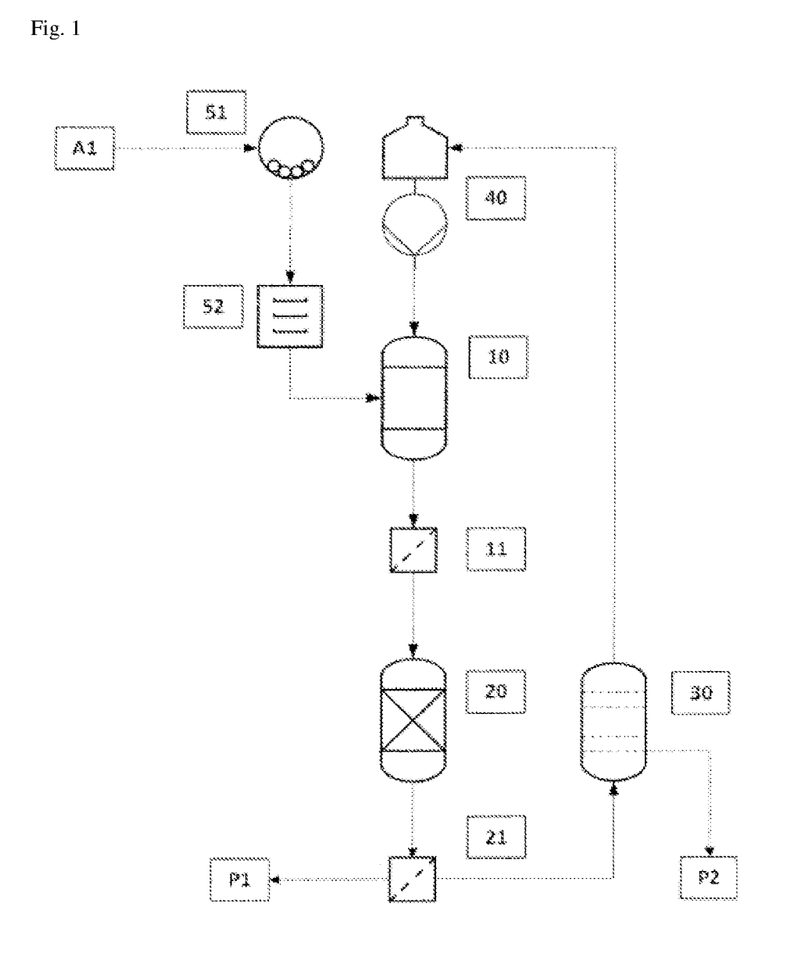
FIG. 1: a schematic representation of a method according to the invention.

In the following, an exemplary implementation of the method according to the invention is to be shown schematically with reference to FIG. 1.

The biomass of microalgae (A1), for example, from Bacillariophyceae or Prymnesiophyceae, is comminuted in an optional method step in a device for the cell disruption of the biomass of algae (51).

In an optional method step, the comminuted biomass of microalgae is then dried in a device for drying the biomass of algae (52), thus producing a particulate biomass of algae.

The particulate biomass of microalgae is transferred to an extraction reactor unit (10) in which, at a pressure of 3 to 100 bar and a temperature of 60 to 150° C., a mixture comprising an algae extract and a biomass of algae subjected to extraction is obtained from the biomass of algae by means of the at least one nonpolar organic solvent, for example, n-hexane.

The biomass of algae subjected to extraction is separated from the algae extract on the way to the precipitation reactor unit (20) by the first filter element (11), which is assigned to the extraction reactor unit (10). The pressure difference between the extraction reactor unit (10) and the precipitation reactor unit (20) is used for the filtration.

The pressure is accordingly reduced to 3 to 20 bar. The pressure in the precipitation reactor unit (20) is then further reduced to 3 to 10 bar and to a temperature of 50 to −80° C., over the course of which fucoxanthin crystals precipitate from the algae extract.

These precipitated fucoxanthin crystals are then separated by means of filtration, in particular using the pressure of 3 to 10 bar present in the precipitation reactor unit (20), through the second filter element (21), wherein a fucoxanthin-crystal-containing precipitate (P1) and a fatty acid-containing algae extract fraction are obtained.

Alternatively, the filtration through the second filter element (21) can be a vacuum filtration, in particular when the pressure in the precipitation reactor unit is reduced to 0 bar. The fatty acid-containing lipid fraction (P2) from this fatty acid-containing algae extract fraction is separated from the at least one nonpolar organic solvent in a further method step by means of distillation in a distillation apparatus (30).

Optionally, the evaporated solvent is cooled again and recirculated in a solvent recycling device (40) in order to be used for another extraction in the extraction reactor.

A specific embodiment of the schematic representation is shown below.

The diatom Phaeodactylum tricornutum (Bacillariophyceae) was used as the biomass of microalgae (A1), which was previously produced in 180 L flat-plate photobioreactors under photoautotrophic conditions in an outdoor pilot plant.

The biomass of algae was comminuted in an agitator ball mill (PML-2, Bühler) with a Centrex S1 grinding chamber and a grinding volume of 0.22 dm$^3$ as a cell disruption device (51). Stabilized ceramic balls (Draison Ytterium Ultra Power, Bühler) with a diameter of 0.3 mm and a density of 5.95 g cm$^{-3}$ were used as grinding media. The algae cells suspended in an aqueous medium were continuously conveyed by a pump (PSF 3, Ragazzini) from a storage container to the grinding chamber of the agitator ball mill. The dissociation degree was checked over a period of 3 hours by measuring the protein content in the supernatant by means of FTIR spectroscopy.

The biomass of algae was then dried under vacuum for a period of 24 hours using a freeze-drying device from the company Christ. The particulate biomass of algae dried in vacuo was then transferred to an extraction reactor unit (10).

A pressure of 100 bar and a temperature of 100° C. were used for the extraction in the extraction reactor unit (10). The residence time during the solid-liquid extraction was 20 minutes. N-hexane was used as the solvent, and a pressure-tight stainless-steel container was used as the extraction reactor unit (10). A sintered stainless-steel filter with a pore size of 0.25 μm was used as the first filter element (11) to separate the biomass of algae subjected to extraction.

The biomass of algae subjected to extraction was separated from the algae extract by the first filter element (11), which is assigned to the extraction reactor unit (10), on the way to the precipitation reactor unit (20) with the pressure being reduced from originally 100 to 30 bar in the precipitation reactor unit.

The pressure in the precipitation reactor unit (20) was then lowered to 3 bar and the temperature to 25° C. with fucoxanthin crystals precipitating from the algae extract in the form of a precipitate.

These precipitated fucoxanthin crystals were then separated by means of filtration, in particular using the pressure of 3 bar in the precipitation reactor unit (20), through the second filter element (21), wherein a fucoxanthin-crystal-containing precipitate and a fatty acid-containing algae extract fraction were obtained. A filter made of polytetrafluoroethylene (PTFE) with a pore size of 1 μm was used as the second filter element (21). The fatty acid-containing lipid fraction from this fatty acid-containing algae extract fraction was separated from the at least one nonpolar organic solvent, n-hexane, in a further method step by means of distillation in a distillation apparatus (30). The n-hexane was then reused in the extraction reactor unit (10) for subsequent operations.

The P. tricornutum biomass of algae used in the example had, based on the total dry matter of the biomass of algae, a total fatty acid content of 104.7 mg/g, an eicosapentaenoic acid (EPA) content of 54.5 mg/g and a fucoxanthin content of 17.6 mg/g.

Figure 2A:
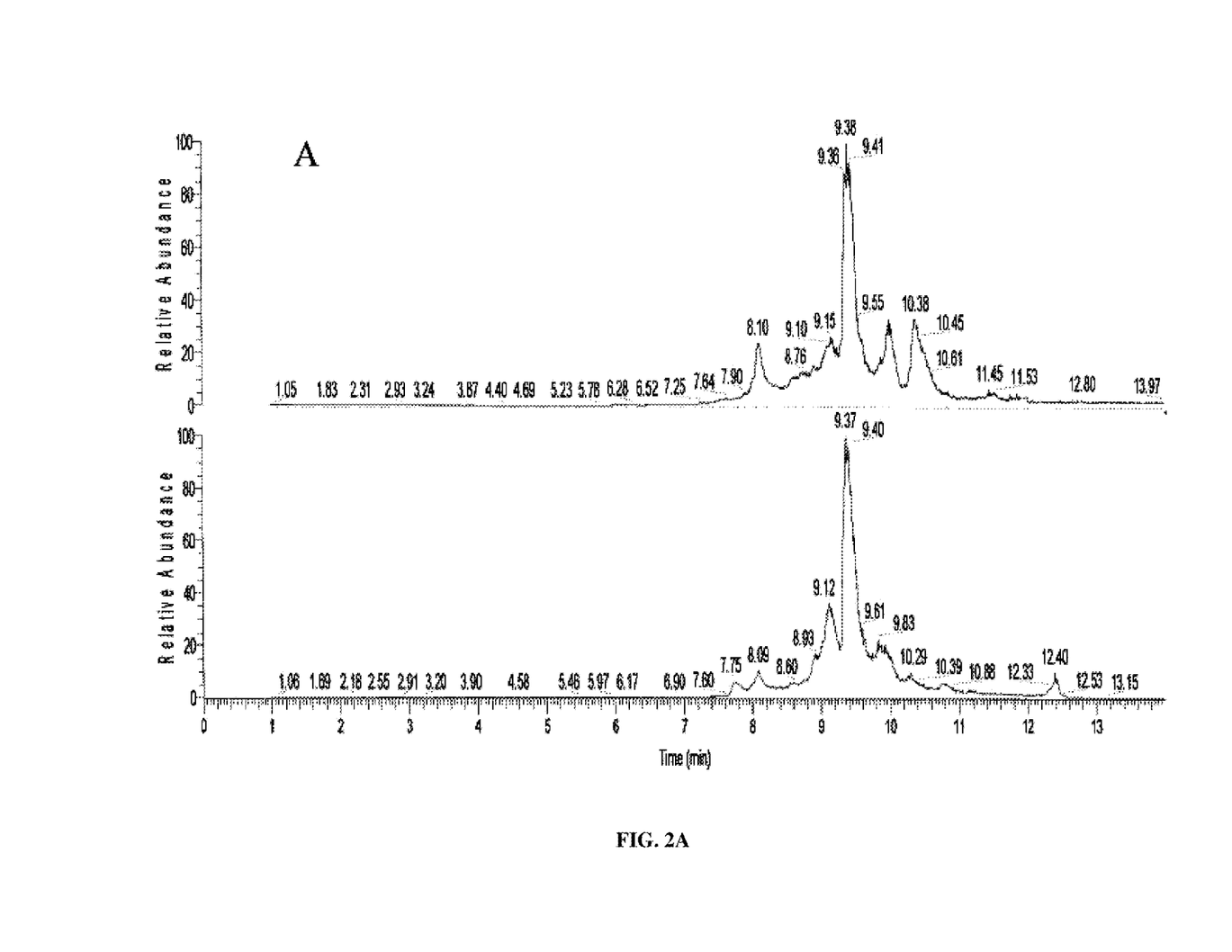
Figure 2B:
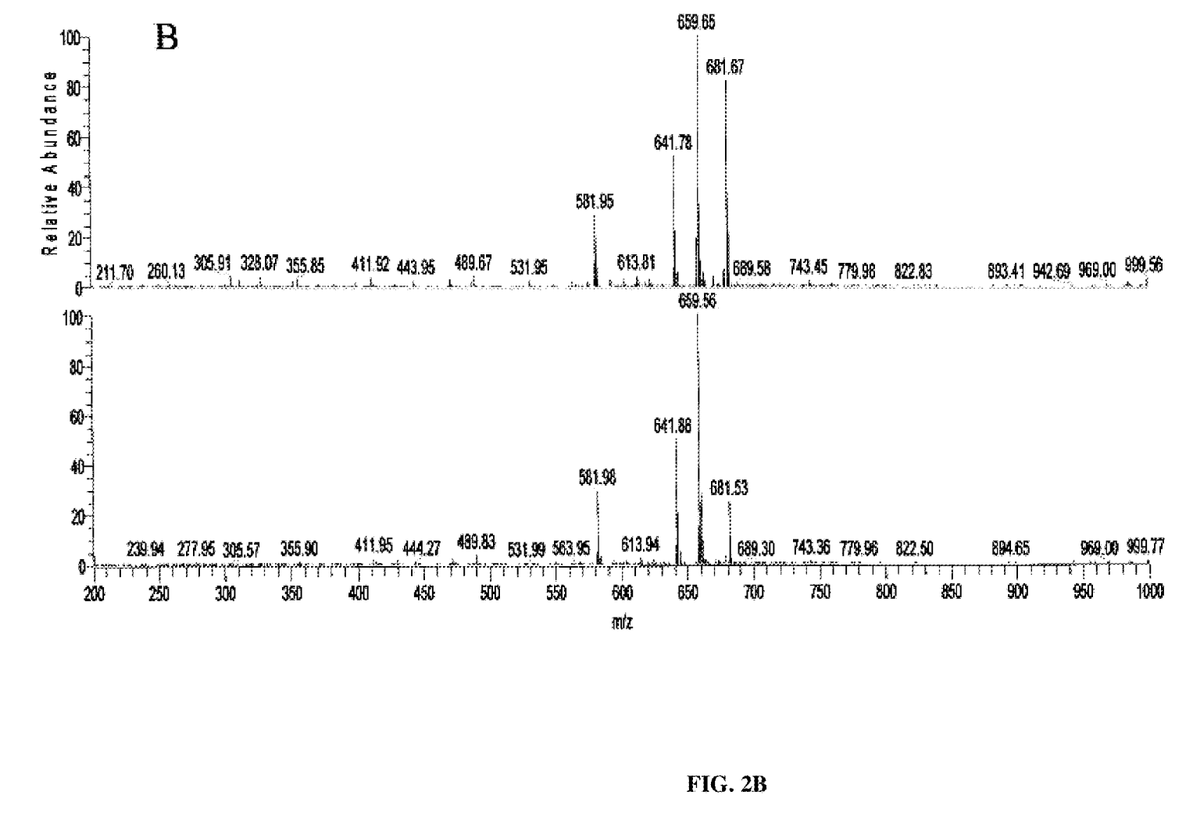
Figure 3:
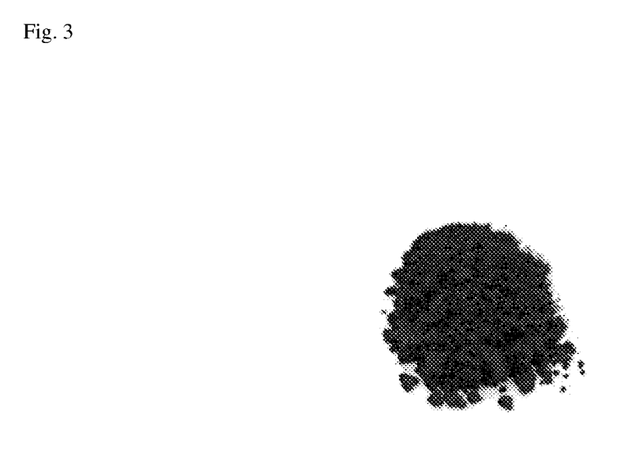
FIG. 3: a representation of fucoxanthin-crystal-containing precipitate from *P. tricornutum* that was obtained and dried according to the invention.
Figure 4A:
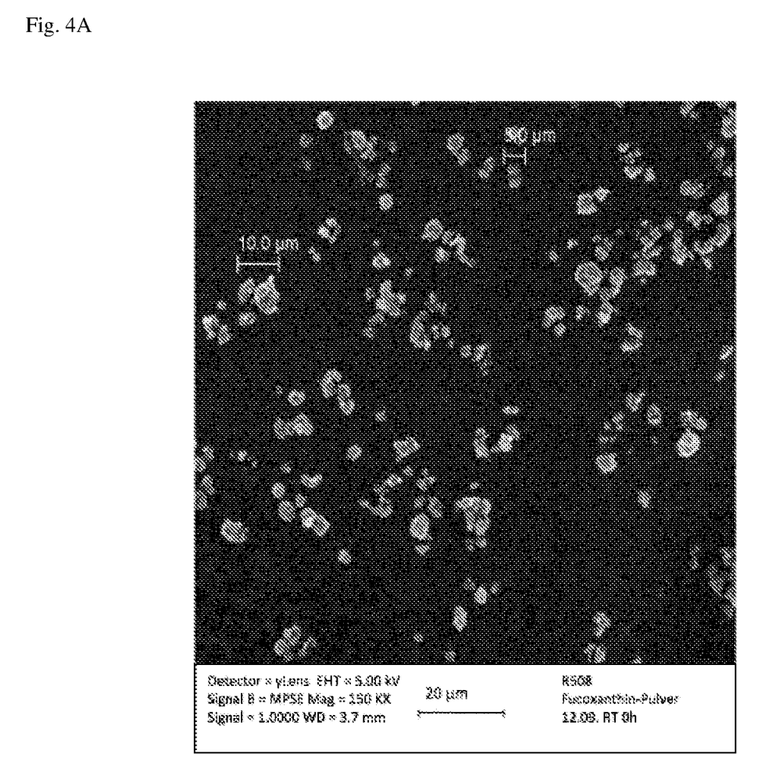
Figure 4B:
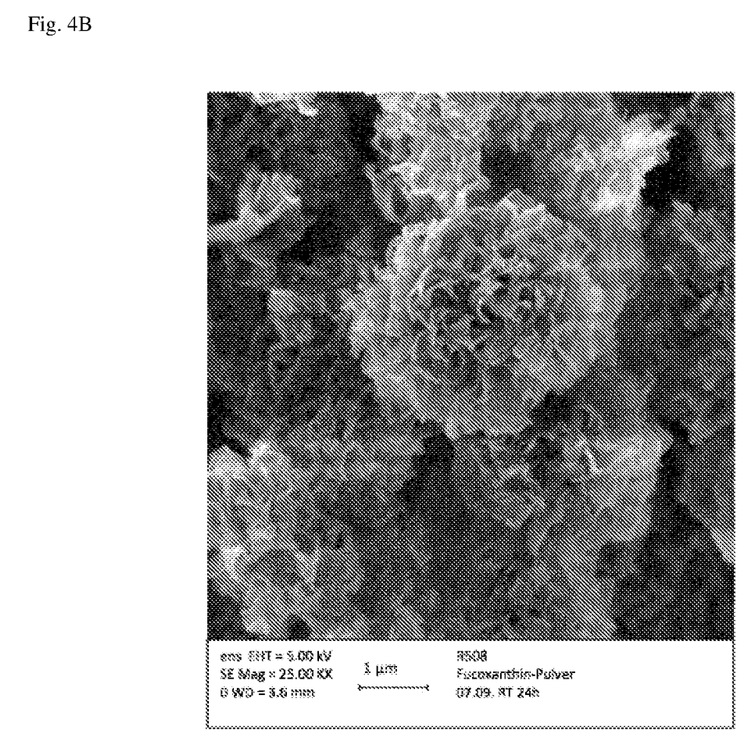
Figure 4C:
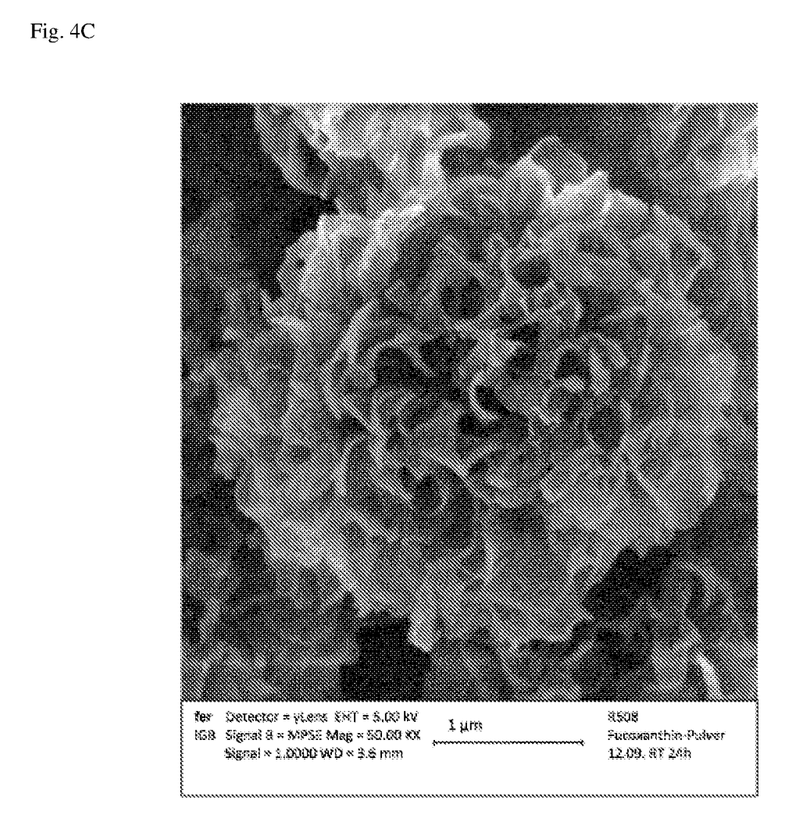

In the example, based on 1 g of the P. tricornutum used, it was possible to obtain 7.1 mg fucoxanthin-crystal-containing precipitate as a fucoxanthin-crystal-containing precipitate (P1) (see FIG. 3). The fucoxanthin-crystal-containing precipitate had individual fucoxanthin crystals (FIGS. 4B and 4C) in the form of agglomerates (FIG. 4A). The fucoxanthin-crystal-containing precipitate had a mass fraction, that is to say a purity, of fucoxanthin of 98.3% by weight (UHPLC-MS) (based on total dry matter) (see FIG.

2). Based on the amount of fucoxanthin available in the starting biomass used, this corresponds to a yield of 40% by weight (DM) (yield based on the dry weight of the fucoxanthin in the starting material).

Based on 1 g of the *P. tricornutum* biomass of algae used, 87.85 mg fatty acids and 49.0 mg eicosapentaenoic acid (EPA) were obtained. Thus, about 55.8% by weight (based on the total weight of the dry matter of fatty acids in the fatty acid-containing lipid fraction) of the fatty acids are in the fatty acid-containing lipid fraction (P2) EPA. Based on the amount of fatty acids available in the starting biomass used, this corresponds to a yield of 83.9% by weight (DM) (yield based on the dry weight of the fatty acids in the starting material). Based on the amount of eicosapentaenoic acid (EPA) available in the starting biomass used, a yield of 89.9% by weight (DM) (yield based on the dry weight of the EPA in the starting material) was achieved. In view of the total dry matter of the fatty acid-containing lipid fraction (P2) of 134 mg (for 1 g of dry biomass), the fatty acids represent a proportion of 65.6% by weight in the fraction (based on total dry matter).

REFERENCES

Airanthi, M. K. W.-A., Hosokawa, M, Miyashita, K., 2011. Comparative Antioxidant Activity of Edible Japanese Brown Seaweeds. J. Food Sci. 76, C104-C111. https://doi.org/10.1111/j.175093841.2010.01915.x Gómez-Loredo, A., Benavides, J., Rito-Palomares, M., 2014. Partition behavior of fucoxanthin in ethanol-potassium phosphate two-phase systems: Partition behavior of fucoxanthin in ethanol-potassium phosphate two-phase systems. J. Chem. Technol. Biotechnol. 89, 1637-1645. https://doi.org/10.1002/jctb.4514

Heo, S.-J., Jeon, Y.-J., 2009. Protective effect of fucoxanthin isolated from Sargassum siliquastrum on UV-B induced cell damage. J. Photochem. Photobiol. B 95, 101-107. https://doi.org/10.1016/j.jphotobiol.2008.11.011

Heo, S.-J., Yoon, W.-J., Kim, K.-N., Oh, C., Choi, Y.-U., Yoon, K.-T., Kang, D.-H., Qian, Z.-J., Choi, I.-W., Jung, W.-K., 2012. Anti-inflammatory effect of fucoxanthin derivatives isolated from Sargassum siliquastrum in lipopolysaccharide-stimulated RAW 264.7 macrophage. Food Chem. Toxicol. 50, 3336-3342. https://doi.org/10.1016/j.fct.2012.06.025

Hosokawa, M., Wanezaki, S., Miyauchi, K., Kurihara, H., Kohno, H., Kawabata, J., Odashima, S., Takahashi, K., 1999. Apoptosis-Inducing Effect of Fucoxanthin on Human Leukemia Cell Line HL-60. Food Sci. Technol. Res. 5, 243-246. https://doi.org/103136/1505243

Kajikawa, T., Okumura, S., Iwashita, T., Kosumi, D., Hashimoto, H., Katsumura, S., 2012. Stereocontrolled Total Synthesis of Fucoxanthin and Its Polyene Chain-Modified Derivative. Org. Lett. 14, 808-811. https://doi.org/10.1021/ol203344c Kim, S. M., Jung, Y.-J., Kwon, O.-N., Cha, K. H., Um, B.-H., Chung, D., Pan, C.-H., 2012a. A Potential Commercial Source of Fucoxanthin Extracted from the Microalga *Phaeodactylum tricornutum*. Appl. Biochem. Biotechnol. 166, 1843-1855. https://doi.org/10.1007/s12010-012-9602-2

Kim, S. M., Kang, S.-W., Kwon, O.-N., Chung, D., Pan, C.-H., 2012b. Fucoxanthin as a major carotenoid in *Isochrysis aff. galbana*: Characterization of extraction for commercial application. J. Korean Soc. Appl. Biol. Chem. 55, 477-483. https://doi.org/10.1007/s13765-012-2108-3

Lee, J. H., O'Keefe, J. H., Lavie, C. J., Harris, W. S., 2009. Omega-3 fatty acids: cardiovascular benefits, sources and sustainability. Nat. Rev. Cardiol. 6, 753-758. https://doi.org/10.1038/nrcardio.2009.188

Maeda, H., Hosokawa, M, Sashima, T., Funayama, K., Miyashita, K., 2005. Fucoxanthin from edible seaweed, Undaria pinnatifida, shows antiobesity effect through UCP1 expression in white adipose tissues. Biochem. Biophys. Res. Commun. 332, 392-397. https://doi.org/10.1016/j.bbrc.2005.05.002

Peng, J., Yuan, J.-P., Wu, C.-F., Wang, J.-H., 2011. Fucoxanthin, a Marine Carotenoid Present in Brown Seaweeds and Diatoms: Metabolism and Bioactivities Relevant to Human Health. Mar. Drugs 9, 1806-1828. https://doi.org/10.3390/md9101806

Pieber, S., Schober, S., Mittelbach, M, 2012. Pressurized fluid extraction of polyunsaturated fatty acids from the microalga Nannochloropsis oculata. Biomass Bioenergy 47, 474-482. https://doi.org/10.1016/j.biombioe.2012.10.019

Xia, S., Wang, K., Wan, L, Li, A., Hu, Q, Zhang, C., 2013. Production, Characterization, and Antioxidant Activity of Fucoxanthin from the Marine Diatom *Odontella aurita*. Mar. Drugs 11, 2667-2681. https://doi.org/10.3390/md11072667

The invention claimed is:

1. A method for obtaining a fucoxanthin-containing precipitate and a fatty acid-containing lipid fraction from a biomass of algae, comprising the steps:
   a) providing at least one nonpolar organic solvent and biomass of algae,
   b) extracting fucoxanthin and fatty acids by means of the at least one non-polar organic solvent provided in method step a) from the biomass of algae provided in method step a) in at least one extraction reactor unit (10), which is assigned to at least one first filter element (11), comprising, at a temperature of 60 to 150° C. and a pressure from 1.5 to 100 bar, a mixture comprising an algae extract and a biomass of algae subjected to extraction,
   c) separating the biomass of algae subjected to extraction from the mixture obtained in method step b) by means of filtration through the at least one first filter (11) element to obtain a filtered algae extract and introduction of the filtered algae extract obtained in at least one precipitation reactor unit (20) to which at least one second filter element (21) is assigned,
   d) lowering the temperature of the filtered algae extract to −80 to 50° C. in the precipitation reactor unit (20) to precipitate fucoxanthin crystals in order to obtain a mixture of fucoxanthin-crystal-containing precipitate and a fatty-acid containing algae extract fraction,
   e) separating the fucoxanthin-crystal-containing precipitate from the mixture of fucoxanthin-crystal-containing precipitate and fatty acid-containing algae extract fraction by means of filtration through the at least one second filter element (21) to obtain a fucoxanthin-crystal-containing precipitate and a fatty acid-containing algae extract fraction, and
   f) separating a fatty acid-containing lipid fraction from the fatty acid-containing algae extract fraction by evaporating the at least one nonpolar organic solvent to obtain the fatty acid-containing lipid fraction.

2. The method according to claim 1, wherein the temperature in step b) is 85 to 120° C.

3. The method according to claim 1, wherein the pressure is lowered in step c) after the extraction has been carried out in method step b).

4. The method according to claim 3, wherein the pressure is reduced to 1 to 30 bar in method step c) after the extraction has been carried out in step b).

5. The method according to claim 1, wherein the pressure is reduced in method step e) after the precipitation has been carried out in step d).

6. The method according to claim 1, wherein the at least one nonpolar organic solvent evaporated in step f) is liquefied in an additional method step g) and the liquid, at least one nonpolar organic solvent, is provided again in step a).

7. The method according to claim 1, wherein the biomass of algae provided in step a) was fed to a cell disruption and/or dried.

8. The method according to claim 1, wherein the biomass of algae provided in step a) is a particulate biomass of algae.

9. The method according to claim 1, wherein the at least one nonpolar organic solvent is an alkane, in particular an n-alkane.

10. The method according to claim 1, wherein the algae extract obtained in step b) comprises further carotenoids, polyphenols and/or phytosterols, which are separated in step f) from the at least one nonpolar organic solvent together with the fatty acid-containing lipid fraction from the fatty acid-containing algae extract fraction.

11. The method according to claim 1, wherein the fucoxanthin crystals obtained in step e) have a diameter of 0.1 to 10 μm in the fucoxanthin-crystal-containing precipitate.

12. The method according to claim 1, wherein the fucoxanthin crystals obtained in step e) are present in the fucoxanthin-crystal-containing precipitate in the form of agglomerates, in particular in a size from 10 to 100 μm.

13. The method according to claim 1, wherein the separation of the fucoxanthin-crystal-containing precipitate in step e) takes place by means of overpressure, underpressure or vacuum-assisted filtration.

14. The method according to claim 1, wherein the residence time in the extraction reactor in step b) is 1 to 60 minutes.

15. The method according to claim 1, wherein the residence time in the precipitation reactor in step d) is 1 to 60 minutes.

16. The method according to claim 1, wherein the at least one extraction reactor unit (10) and/or the at least one precipitation reactor unit (20) is a fluidized bed reactor or are fluidized bed reactors.

17. The method according to claim 1, wherein the fatty acid-containing lipid fraction obtained in step f) has 50 to 70% by weight EPA (based on the total weight of the dry matter of fatty acids in the fatty acid-containing lipid fraction).

18. The method according to claim 1, wherein the fatty acid-containing lipid fraction obtained in step f) has 50 to 70% by weight DHA (based on the total weight of the dry matter of fatty acids in the fatty acid-containing lipid fraction).

* * * * *